(12) United States Patent
Consigny

(10) Patent No.: US 8,747,354 B1
(45) Date of Patent: Jun. 10, 2014

(54) CATHETER FOR THE LOCAL DELIVERY OF THERAPEUTIC AGENTS

(75) Inventor: Paul M. Consigny, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 189 days.

(21) Appl. No.: 11/982,686

(22) Filed: Nov. 2, 2007

(51) Int. Cl.
*A61M 29/00* (2006.01)

(52) U.S. Cl.
USPC ........ 604/104; 604/96.01; 604/105; 604/106; 604/107; 604/164.03; 604/164.13; 606/191; 606/194; 606/198; 606/200

(58) Field of Classification Search
USPC ............ 604/104–107, 164.03, 164.13, 96.01; 606/191, 198, 108, 151, 159, 194, 200
See application file for complete search history.

(56) References Cited

U.S. PATENT DOCUMENTS

| | | | | | |
|---|---|---|---|---|---|
| 4,706,671 | A | * | 11/1987 | Weinrib | 606/159 |
| 5,071,407 | A | * | 12/1991 | Termin et al. | 604/104 |
| 5,451,408 | A | * | 9/1995 | Mezei et al. | 424/450 |
| 5,800,525 | A | * | 9/1998 | Bachinski et al. | 623/1.1 |
| 6,129,739 | A | * | 10/2000 | Khosravi | 606/200 |
| 6,203,561 | B1 | * | 3/2001 | Ramee et al. | 606/200 |
| 6,592,616 | B1 | | 7/2003 | Stack et al. | |
| 6,645,135 | B1 | | 11/2003 | Bhat | |
| 6,676,682 | B1 | * | 1/2004 | Tsugita et al. | 606/200 |
| 8,114,114 | B2 | * | 2/2012 | Belson | 606/200 |
| 2003/0109824 | A1 | * | 6/2003 | Anderson et al. | 604/104 |
| 2004/0199201 | A1 | * | 10/2004 | Kellett et al. | 606/200 |

OTHER PUBLICATIONS

Gal et al., "Selection of a RNA aptamer that binds to human activated Protein C and inhibits its protease function", Eur. J. Biochem. 252, pp. 553-562 (1998).
Hasenstab et al., "Tissue Factor Overexpression in Rat Arterial Neointima Models Thrombosis and Progression of Advanced Atherosclerosis", Circulation 101, pp. 2651-2657 (2000).
Jander et al., "Expression of Tissue Factor in High-Grade Carotid Artery Stenosis, Association With Plaque Destabilization", Stroke 32, pp. 850-854 (2001).
Kaikita et al., "Tissue Factor Expression on Macrophages in Coronary Plaques in Patients With Unstable Angina", Arterioscl. Thromb Vasc Biol. 17, pp. 2232-2237 (1997).
Libby et al. "Stabilization of Atherosclerotic Plaques: New Mechanisms and Clinical Targets", Nature Med 8, pp. 1257-1262 (2002).
Rusconi et al., "RNA aptamers as reversible antagonists of coagulation factor IXa", Nature 419, pp. 90-94 (2002).
Speidel et al., "Tissue Factor Mediates Prolonged Procoagulant Activity on The Luminal Surface of Balloon-Injured Aortas in Rabbits", Circulation vol. 92, No. 11, pp. 3323-3330 (1995).
Toschi et al., "Tissue Factor Modulates The Thrombogenicity of Human Atherosclerotic Plaques", Circulation vol. 95, pp. 594-599 (1997).
Tuddenham "RNA as drug and antidote", Nature 419, pp. 23-24 (2002).
White et al., "Developing aptamers into therapeutics", J. Clin. Invest. vol. 106, No. 8, pp. 929-934 (2000).
Wilcox et al., "Localization of tissue factor in the normal vessel wall and in the atherosclerotic plaque", Proc. Natl. Acad. Sci 86: 2839-43 (1989).

* cited by examiner

*Primary Examiner* — Quynh-Nhu H Vu
*Assistant Examiner* — Larry R Wilson
(74) *Attorney, Agent, or Firm* — Squire Sanders (US) LLP

(57) ABSTRACT

A catheter for the local delivery of therapeutic agents and methods of using the same for the treatment or prevention of disease are disclosed. A catheter may include a tubular net and a guidewire attached to the tubular net longitudinally along the abluminal side of the net. The catheter may further include a tubular member that opens onto the abluminal side of the tubular net.

24 Claims, 2 Drawing Sheets

CATHETER FOR THE LOCAL DELIVERY OF THERAPEUTIC AGENTS

FIELD OF THE INVENTION

The present invention is directed to a catheter for the local delivery of therapeutic agents and methods of using the same for the treatment of vascular disease.

BACKGROUND OF THE INVENTION

Coronary heart disease is generally thought to be caused by the narrowing of coronary arteries by atherosclerosis, i.e., the buildup of fatty deposits in the lining of the arteries. The process that may lead to atherosclerosis begins with the accumulation of excess fats and cholesterol in the blood. These substances infiltrate the lining of arteries, gradually increasing in size to form deposits commonly referred to as plaque or atherosclerotic occlusions. Plaques narrow the arterial lumen and impede blood flow. Blood cells may collect around the plaque, eventually creating a blood clot that may block the artery completely.

While the known procedures for treating plaque have gained wide acceptance and shown good efficacy for treatment of standard stenotic plaques, they may be ineffective, and possibly dangerous, when thrombotic conditions are superimposed on atherosclerotic plaques.

Tissue factor has been implicated in plaque/vascular thrombosis. For example, in human carotid plaque, tissue factor is co-localized with areas of plaque inflammation, predominantly to macrophages.

Tissue factor acts by activating Factor VII which activates Factor X that stimulates the conversion of prothrombin (II) into thrombin (IIa). Thrombin then acts to convert fibrinogen to fibrin monomer which then polymerizes to form a fibrin clot.

Because thrombosis causes most manifestations of atheroma, therapies that block thrombosis in a particular region of the vasculature are needed. The present invention provides such a therapy, as well as a novel method of administering the therapy.

SUMMARY OF THE INVENTION

The present invention relates to a catheter that includes an elongate tubular sheath comprising a proximal end, a distal end and a lumen extending from the proximal end to the distal end, an elongate tubular net operatively coupled to the elongate tubular sheath, the tubular net comprising a proximal end, a distal end and a lumen extending from the proximal end to the distal end and further comprising expandable hoops positioned around the circumference of the distal and proximal ends of the net and a guidewire attached to the elongate tubular net longitudinally along the abluminal side of the net, wherein a distal end of the guidewire is attached to the distal end of the elongate tubular net at a point other than longitudinally along the abluminal side of the net.

In various aspects, the elongate tubular net is extendable and retractable such that in its retracted position the net is disposed within the lumen of the elongate tubular sheath and in its extended position the net extends beyond the distal end of the elongate tubular sheath where it expands to its tubular shape.

In various aspects, the elongate tubular sheath further includes an elongate tubular member comprising a proximal end, a distal end and a lumen extending from the proximal end to the distal end disposed within the lumen of the elongate tubular sheath, wherein the distal end of the elongate tubular member opens onto the abluminal side of the proximal end of the elongate tubular net when the elongate tubular net is in its extended position.

In various aspects, the elongate tubular net can be made of a material selected from a group that includes polyethylene, expanded polytetrafluoroethylene, nylon and nitinol.

In various aspects, the elongate tubular net has low porosity.

In various aspects, the elongate tubular net tapers to a point at its distal end and has a porosity sufficient to allow blood to flow through it.

In various aspects, the expandable hoops can include an elastic material. In these aspects, the elastic material can include polyethylene, nylon, nitinol or polyvinylchloride.

Another aspect of the invention relates to a method for treating or preventing a vascular disease. The method involves providing the catheter according to the invention, inserting the catheter into the blood vessel of a patient, deploying the elongate tubular net, providing a bioactive agent formulation and introducing the bioactive agent formulation into the blood vessel of a patient through the catheter.

In various aspects, the viscosity of the bioactive agent formulation is modified by an excipient. In these aspects, the excipient can be selected from a group that includes a polymer, a protein, a sugar and an alcohol.

In various aspects, the bioactive agent formulation can include a hydrophilic solution or an oil emulsion. In other aspects, the bioactive agent formulation can include a cell permeating agent. In other aspects, the bioactive agent formulation can include an inhibitor of tissue factor activity. In further aspects, the bioactive agent formulation can include a tissue factor pathway inhibitor or a tissue factor aptamer.

In various aspects, the vascular disease is selected from a group that includes atherosclerosis, restenosis, vulnerable plaque, peripheral arterial disease, arterial thrombosis, venous thrombosis and deep vein thrombosis.

DETAILED DESCRIPTION

Figure 1:
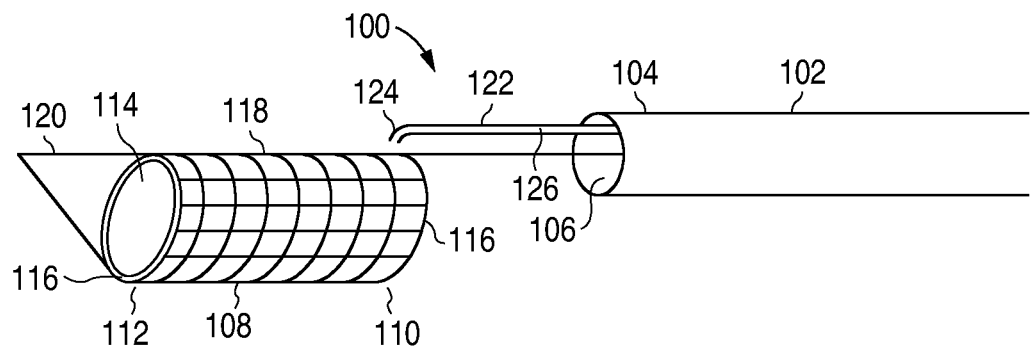
FIG. 1 is a side view of a catheter of the invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the claims. For clarity, like components are designated by like reference numerals throughout the various accompanying figures.

DEFINITIONS

As used herein, "lumen" refers to a cavity of a tubular structure including an organ such as a blood vessel or a device such as a catheter.

As used herein, "abluminal" refers to a location including and exterior to the outer surface of a tubular structure.

As used herein, "operatively coupled" refers to the attachment of the elongate tubular net to the elongate tubular sheath through either direct or indirect means.

As used herein, "guide wire" refers to a wire used to direct the placement of a catheter at a site of interest as well as a wire used to deploy the elongate tubular net once the catheter is in position in the vasculature.

As used herein, "porosity" refers to the property of a net of the invention that allows or does not allow fluid, e.g., blood, to move through it. For example, a high porosity net will allow blood to move freely through it whereas blood will move more slowly or not at all through a low porosity net.

As used herein, "patient" refers to any organism that can benefit from the administration of a drug, e.g., a tissue factor inhibitor. In particular, patient refers to a mammal such as a cat, dog, horse, cow, pig, sheep, rabbit, goat or a human being.

As used herein, "treating" refers to the administration of a therapeutically effective amount of a drug to a patient known or suspected to be suffering from a vascular disease. Presently preferred drugs useful with this invention include, but are not limited to, tissue factor inhibitors.

As used herein, "therapeutically effective amount" refers to the amount of drug that has a beneficial effect, which may be curative or palliative, on the health and well-being of a patient with regard to a vascular disease with which the patient is known or suspected to be afflicted. A therapeutically effective amount may be administered as a single bolus, as intermittent bolus charges, as short, medium or long term sustained release formulations or as any combination of these.

As used herein, "known" to be afflicted with a vascular disease refers first to a condition that is relatively readily observable and or diagnosable. An example, without limitation, of such a disease is atherosclerosis, which is a discrete narrowing of a patient's arteries. Restenosis, on the other hand, while in its latter stages, like atherosclerosis, is relatively readily diagnosable or directly observable, may not be so in its nascent stage. Thus, a patient may be "suspected" of being afflicted or of being susceptible to affliction with restenosis at some time subsequent to a surgical procedure to treat an atherosclerotic lesion.

As used herein, "atherosclerosis" refers to the condition in which fatty substances, cholesterol, cellular waste products, calcium and/or fibrin are deposited on the inner lining or intima of an artery.

As used herein, "restenosis" refers to the re-narrowing or blockage of an artery at or near the site where angioplasty or another surgical or interventional procedure was previously performed to remove a stenosis.

As used herein, "peripheral arterial disease" refers to a condition similar to coronary artery disease and carotid artery disease in which fatty deposits build up in the inner linings of the artery walls thereby restricting blood circulation, mainly in arteries leading to the kidneys, stomach, arms, legs and feet.

Vulnerable plaque on the other hand is quite different from either atherosclerosis or restenosis. Vulnerable plaque occurs primarily within the wall of a vessel and does not cause prominent protrusions into the lumen of the vessel. It is often not until it is "too late," i.e., until after a vulnerable plaque has broken and released its components into the vessel, that its presence is even known. Numerous methods have and are being investigated for the early diagnosis of vulnerable plaque but to date none have proven completely successful.

As used herein, "arterial thrombosis" refers to a blood clot (thrombus) within an artery.

As used herein, "venous thrombosis" refers to a blood clot within a vein.

As used herein, "deep vein thrombosis" refers to a blood clot that develops in a deep vein, usually in the lower leg.

As used herein, "excipient" refers to a chemically inert substance that can be used as a bioactive agent carrier.

As used herein, "viscosity" refers to a fluid's resistance to flow. For example, a fluid with a high viscosity will flow more slowly than a fluid with a low viscosity.

The present invention relates to catheter 100 that includes elongate tubular sheath 102 comprising distal end 104 and lumen 106 extending through elongate tubular sheath 102 to the distal end, elongate tubular net 108 operatively coupled to elongate tubular sheath 102, tubular net 108 comprising proximal end 110, distal end 112 and lumen 114 extending from proximal end 110 to distal end 112 and further comprising expandable hoops 116 positioned around the circumference of the distal and proximal ends of net 108. Catheter 100 also includes guidewire 118 attached to elongate tubular net 108 longitudinally along the abluminal side of net 108, wherein distal end 120 of guidewire 118 is attached to distal end 112 of elongate tubular net 108 at a point other than longitudinally along the abluminal side of net 108.

Elongate tubular net 108 is extendable and retractable such that in its retracted position net 108 is disposed within lumen 106 of elongate tubular sheath 102 and in its extended position net 108 extends beyond distal end 104 of elongate tubular sheath 102 to expand into its tubular shape. Guidewire 118 can be used to extend and retract elongate tubular net 108 for easy deployment in a blood vessel.

Elongate tubular sheath 102 can further include elongate tubular member 122 that has distal end 124 and lumen 126 extending through elongate tubular member 122 to distal end 124 and disposed within lumen 106 of elongate tubular sheath 102. Distal end 124 of elongate tubular member 122 opens onto the abluminal side of proximal end 110 of elongate tubular net 108 when elongate tubular net 108 is in its extended position.

Figure 2A:
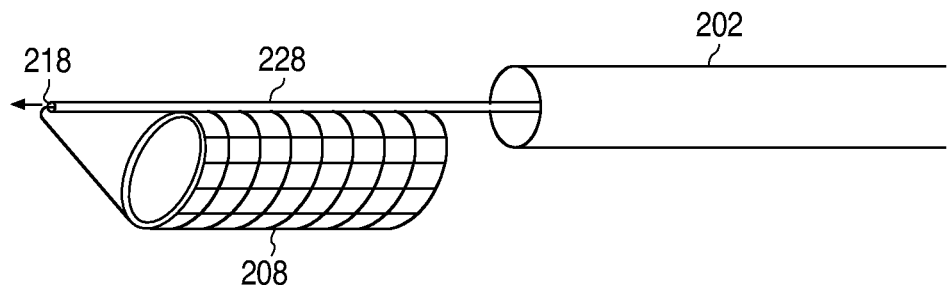
FIGS. 2A-B are a side view of various embodiments of the catheter of the invention.
Figure 2B:
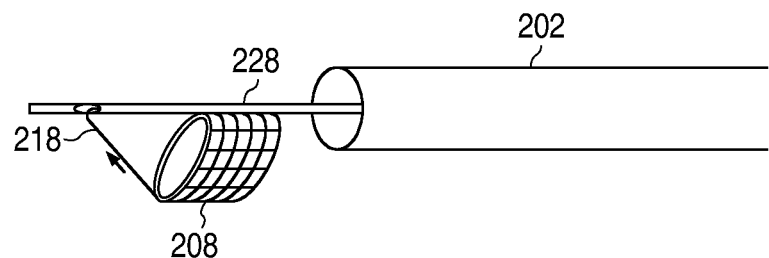

FIGS. 2A-B illustrate other embodiments for deploying elongate tubular net 208 in a vessel. FIG. 2A illustrates one embodiment in which elongate tubular net 208 is attached longitudinally along elongate cylindrical tube 228, through which guidewire 218 runs. When guidewire 218 is pushed through elongate cylindrical tube 228, the direction being depicted by the arrow, elongate tubular net 208 will expand. It is to be understood that elongate tubular net 208 and elongate cylindrical tube 228 can both be positioned within elongate tubular sheath 202 prior to deployment. FIG. 2B illustrates another embodiment in which elongate tubular net 208 is attached longitudinally along elongate cylindrical tube 228, through which guidewire 218 runs. In this embodiment, when guidewire 218 is pulled through elongate cylindrical tube 228, the direction being depicted by the arrow, elongate tubular net 208 will collapse.

Elongate tubular net 108 can be made of, although is not limited to, self-expanding and pliable materials including polyethylene, expanded polytetrafluoroethylene, nylon and nitinol.

In various aspects of the invention, elongate tubular net 108 has low porosity. Thus, when a bioactive agent formulation is administered to the abluminal side of elongate tubular net 108 from distal end 124 of elongate tubular member 122, the bioactive agent formulation will concentrate on the outside of elongate tubular net 108 so that it is in direct contact with the vessel wall.

Figure 3:
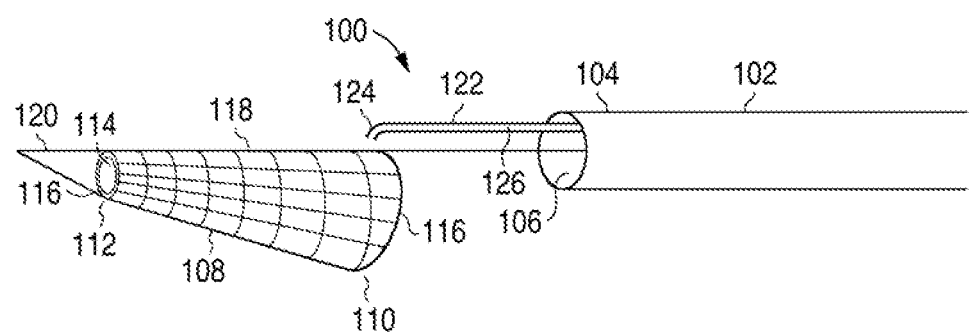
FIG. 3 is a side view of a catheter of the invention.

In one aspect of the invention, elongate tubular net 108 tapers to a point at its distal end, as shown in FIG. 3. In this aspect, the distal end of elongate tubular net 108 has a porosity sufficient to allow blood to flow through it.

In the various aspects of the invention, expandable hoops 116 will be composed of an elastic material so that when elongate tubular net 108 is in its extended position it will expand to line the circumference of the blood vessel in which it is positioned. The elastic material can include, but is not limited to, polyethylene, nylon, nitinol or polyvinylchloride.

Another aspect of the invention relates to a method for treating or preventing a vascular disease including, but not limited to, atherosclerosis, restenosis, vulnerable plaque, peripheral arterial disease, arterial thrombosis, venous thrombosis and deep vein thrombosis, including stent-induced thrombosis.

The method involves inserting catheter 100 into the blood vessel of a patient, deploying elongate tubular net 108 and introducing the bioactive agent formulation into the blood vessel of a patient through catheter 100. In one aspect, the bioactive agent formulation will be introduced onto the proximal abluminal side of net 108 via distal end 124 of elongate tubular member 122.

The bioactive agent formulation can be modified by an excipient, such as, but not limited to, a polymer, a protein, a sugar or an alcohol. The bioactive agent formulation can be a hydrophilic solution or an oil emulsion and/or it can include a cell permeating agent.

Excipients and cell permeating agents are known to those skilled in the art and are encompassed by the present invention.

The bioactive formulation can include a drug or a therapeutic agent that can be an antiproliferative agent, an anti-inflammatory agent, an antineoplastic, an antimitotic, an anti-platelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist or an antioxidant, examples of which are all known to those skilled in the art.

In presently preferred aspects of the invention, the bioactive agent formulation includes an inhibitor of tissue factor activity such as, for example, a tissue factor pathway inhibitor or a tissue factor aptamer.

Tissue Factor pathway inhibitor (TFPI) is a single-chain polypeptide which can reversibly inhibit Factor Xa (Xa). While Xa is inhibited, the Xa-TFPI complex can subsequently also inhibit the FVIIa-TF complex. TFPI contributes significantly to the inhibition of Xa in vivo, despite being present at concentrations of only about 2.5 nM. An exemplary TFPI includes, but is not limited to, tifacogin.

Tissue Factor aptamers are single stranded nucleic acids (DNA or RNA) that directly inhibit tissue factor function by folding into a specific three-dimensional structure with high-affinity binding for the tissue factor protein. Methods for creating apatmers are known to those skilled in the art and are encompassed by the present invention. An exemplary method includes the creation of a combinatorial library of randomized short RNA or DNA ligands of approximately 20-40 nucleotides, incubating the library with tissue factor and then collecting the RNA or DNA molecules that bind to the protein. The bound RNA molecules are amplified using reverse transcriptase polymerase chain reactions (rtPCR) and the bound DNA molecules are amplified using PCR. The steps are repeated, usually around 8-12 times, using conditions known in the art to increase the stringency of binding. The bound RNA and DNA molecules are sequenced and then tested for their ability to inhibit tissue factor activity. The RNA or DNA molecules with the highest affinity and greatest tissue factor inhibitory activity are then selected and used with the methods of the present invention.

Once a suitable tissue factor aptamer is identified, it can be modified to improve its bioavailability. Such modifications include, but are not limited to, using modified RNA oligonucleotides such as 2'-amino, 2'-fluoro or 2'-O-alkyl nucleotides, capping the 3' end to protect from exonuclease degradation, substituting ribose and deoxyribose nucleotides with modified nucleotides or non-nucleotide linkers in order to prevent endonuclease degradation, e.g., using a phosphodiester/phosphorothioate backbone and attachment of the aptamer to a particle such as a liposome or nanoparticle.

Direct inhibitors of tissue factor are also encompassed by the present invention and include, without limitation, a recombinant tissue factor and TNX-832 and Suno-CH36, both of which are chimeric IgG4 antibodies that bind to tissue factor.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

What is claimed is:

1. A catheter comprising:
   an elongate tubular sheath comprising a proximal end, a distal end and a lumen extending from the proximal end to the distal end;
   an elongate tubular net operatively coupled to the elongate tubular sheath, the elongate tubular net comprising a proximal end, an open distal end and a lumen extending from the proximal end to the open distal end and further comprising a distal expandable hoop positioned around the circumference of the open distal end of the elongate tubular net and a proximal expandable hoop positioned around the circumference of the proximal end of the elongate tubular net;
   a guidewire having a portion attached to the elongate tubular net longitudinally across a side of the elongate tubular net, wherein a distal end of the guidewire is attached to the open distal end of the elongate tubular net at a point that allows movement of the guidewire to expand or collapse the elongate tubular net, and
   an elongate tubular member comprising a proximal end, a distal end, and a lumen extending from the proximal end to the distal end of the elongate tubular member, the lumen of the elongate tubular member configured to deliver and discharge a bioactive agent formulation onto the elongate tubular net.

2. The catheter according to claim 1, wherein the elongate tubular net is extendable and retractable such that in its retracted position the elongate tubular net is disposed within the lumen of the elongate tubular sheath and in its extended position the elongate tubular net extends beyond the distal end of the elongate tubular sheath where it expands to its tubular shape.

3. The catheter according to claim 2, wherein the elongate tubular member is at least partially disposed within the lumen of the elongate tubular sheath, wherein the distal end of the elongate tubular member has an opening disposed over an abluminal side of the proximal end of the elongate tubular net when the elongate tubular net is in its extended position.

4. The catheter according to claim 1, wherein the elongate tubular net comprises a material selected from the group consisting of polyethylene, expanded polytetrafluoroethylene, nylon and nitinol.

5. The catheter according to claim 1, wherein the elongate tubular net has low porosity.

6. The catheter according to claim 1, wherein the elongate tubular net tapers to a point at its open distal end and has a porosity sufficient to allow blood to flow through it.

7. The catheter according to claim 1, wherein the expandable hoops comprise an elastic material.

8. The catheter according to claim 7, wherein the elastic material comprises polyethylene, nylon, nitinol or polyvinylchloride.

9. A method for treating or preventing a vascular disease comprising:
providing the catheter according to claim 1;
inserting the catheter into the blood vessel of a patient;
deploying the elongate tubular net;
providing a bioactive agent formulation; and
introducing the bioactive agent formulation into the blood vessel of a patient through the elongate tubular member.

10. The method according to claim 9, wherein the viscosity of the bioactive agent formulation is modified by an excipient.

11. The method according to claim 10, wherein the excipient is selected from the group consisting of a polymer, a protein, a sugar and an alcohol.

12. The method according to claim 9, wherein the bioactive agent formulation comprises a hydrophilic solution or an oil emulsion.

13. The method according to claim 9, wherein the bioactive agent formulation comprises a cell permeating agent.

14. The method according to claim 9, wherein the bioactive agent formulation comprises an inhibitor of tissue factor activity.

15. The method according to claim 9, wherein the bioactive agent formulation comprises tissue factor pathway inhibitor or a tissue factor aptamer.

16. The method according to claim 9, wherein the vascular disease is selected from the group consisting of atherosclerosis, restenosis, vulnerable plaque, peripheral arterial disease, arterial thrombosis, venous thrombosis and deep vein thrombosis.

17. The method according to claim 9, further comprising collapsing the elongate tubular net by inducing movement of the point of attachment between the open distal end of elongate tubular net and the distal end of the guidewire.

18. The method according to claim 9, further comprising expanding the elongate tubular net by inducing movement of the point of attachment between the open distal end of elongate tubular net and the distal end of the guidewire.

19. The catheter according to claim 1, wherein the side of the elongate tubular net attached to the guidewire portion is an abluminal side of the elongate tubular net.

20. The method according to claim 9, further comprising collapsing the elongate tubular net by pulling the guidewire or expanding the elongate tubular net by pushing the guidewire.

21. The catheter according to claim 1, wherein the distal end of the elongate tubular member has a discharge opening disposed outside of the lumen of the elongate tubular sheath and disposed between a proximal edge of the elongate tubular net and a distal edge of the elongate tubular net.

22. The catheter according to claim 1, wherein the elongate tubular net is a low porosity net, and blood will not move at all through the low porosity net.

23. The catheter according to claim 22, wherein blood is capable of flowing through the lumen extending from the proximal end to the open distal end of the elongate tubular net.

24. The method according to claim 9, wherein introducing the bioactive agent formulation into the blood vessel comprises discharging the bioactive agent formulation at a point between a wall of the blood vessel and a lumen wall of the elongate tubular net.

\* \* \* \* \*